United States Patent [19]

Daluge et al.

[11] Patent Number: 4,590,271

[45] Date of Patent: May 20, 1986

[54] 2,4-DIAMINO-5-(SUBSTITUTED)PYRIMI-DINES, USEFUL AS ANTIMICROBIALS

[75] Inventors: Susan M. Daluge, Chapel Hill, N.C.; Paul M. Skonezny, Clay, N.Y.; Barbara Roth, Chapel Hill; Barbara S. Rauckman, Durham, both of N.C.

[73] Assignee: Burroughs Wellcome Co., Research Triangle Park, N.C.

[21] Appl. No.: 490,196

[22] Filed: Apr. 29, 1983

[30] Foreign Application Priority Data

May 1, 1982 [GB] United Kingdom ............... 8212727
May 7, 1982 [GB] United Kingdom ............... 8213248

[51] Int. Cl.$^4$ ................ C07D 239/49; C07D 401/06; C07D 405/06; A61K 31/505
[52] U.S. Cl. ............................. 544/324; 514/252; 514/255; 514/275; 514/326; 544/114; 544/295; 544/325; 548/465; 548/503; 549/49; 549/58; 549/462; 549/467
[58] Field of Search ........... 544/325, 324; 424/252; 514/275

[56] References Cited

U.S. PATENT DOCUMENTS 3,819,629 6/1974 Roth et al. ..................... 544/325
4,039,543 8/1977 Kompis et al. ................. 544/325
4,438,267 3/1984 Daluge et al. .................. 544/325

FOREIGN PATENT DOCUMENTS 2087881 6/1982 United Kingdom ............... 424/251

OTHER PUBLICATIONS

Mazurczak, Chemical Abstract, vol. 89, pp. 656-657, 24352e (1978).
Daluge, Chem. Abst., vol. 97, 1982, pp. 729, 730, 127652x, equi. to UK 2087881.

Primary Examiner—Donald G. Daus
Assistant Examiner—Cecilia Shen
Attorney, Agent, or Firm—Donald Brown

[57] ABSTRACT

Compounds of the formula (II)

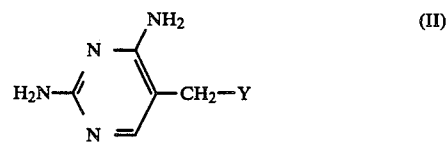

or a salt, N-oxide or acyl derivative thereof, wherein Y is a group

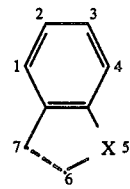

which is linked to the pyrimidinylmethyl moiety at the 1 or 7-position and is optionally substituted at the 2, 3, 4 or 6-position or at the 7-position when the linkage to the pyrimidinylmethyl moiety is at the 1-position wherein X is an oxygen or sulphur atom, a group $CH_2$, a group $S(O)_n$ where n=1 or 2, a group $NR^1$ wherein $R^1$ is hydrogen $C_{1-4}$ alkyl or a group $COR^2$ where $R^2$ is hydrogen, $C_{1-4}$ alkoxy or amino and the dotted line represents a single or double bond, have antimicrobial activity. Processes for making these compounds, pharmaceutical compositions containing them and the medical use of the compounds are also disclosed.

4 Claims, No Drawings

2,4-DIAMINO-5-(SUBSTITUTED)PYRIMIDINES, USEFUL AS ANTIMICROBIALS

The present invention relates to novel 2,4-diamino-5-(substituted)pyrimidines, to pharmaceutical compositions containing them, to processes for preparing them and their compositions, to intermediates for making them and to their use in the treatment of microbial infections.

Certain 2,4-diamino-5-benzylpyrimidines have been demonstrated to be potent inhibitors of dihydrofolate reductase (DHFR) which catalyses the reduction of dihydrofolic acid to tetrahydrofolic acid (THFA). This property has been shown frequently to result in useful pharmaceutical properties particularly in the treatment of bacterial infections. Thus, U.K. Patent specification No. 875,562 discloses inter alia 2,4-diamino-5-benzylpyrimidines wherein the benzyl moiety is substituted by three $C_{1-4}$ alkoxy groups.

Trimethoprim, 2,4-diamino-5-(3,4,5-trimethoxybenzyl)pyrimidine, is specifically disclosed in U.K. Pat. No. 875,562 and is the most active general antibacterial agent amongst the 2,4-diamino-5-benzylpyrimidines known to date. Due to their mode of action, these benzylpyrimidines potentiate the antibacterial activity of the sulphonamides and trimethoprim has been used extensively over the last decade in human therapy in combination with various sulphonamides, and in particular with sulphamethoxazole, for the treatment of bacterial infections.

European Patent application No. 81109631.2 discloses compounds of the formula (I):

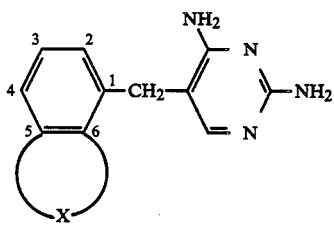

or a salt, N-oxide or acyl derivative thereof, wherein $\widehat{X}$ is a six membered ring optionally containing a hetero atom, both the phenyl ring and the $\widehat{X}$ ring being optionally substituted except that when $\widehat{X}$ does not contain a hetero atom either or both the phenyl ring or $\widehat{X}$ must be substituted other than solely by a hydroxy group at the 4-position of the phenyl ring, and; that there are no substituents attached to the atom of $\widehat{X}$ adjacent to the 6-position of the phenyl ring.

It has now been found that a further group of novel 2,4-diamino-5-(substituted)pyrimidines has advantageous properties for the treatment of microbial infections.

Accordingly, the present invention provides a compound of the formula (II):

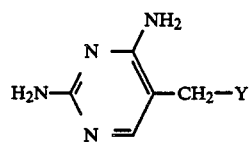

or a salt, acyl derivative or N-oxide thereof wherein Y is a group

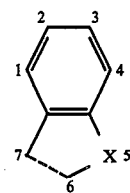

which is linked to the pyrimidinylmethyl moiety at the 1 or 7 position and is optionally substituted at the 2,3,4 or 6 positions or at the 7 position when the linkage to the pyrimidinyl moiety is at the 1 position wherein X is an oxygen or sulphur atom, a group $CH_2$, a group $S(O)_n$ where $n=1$ or 2, or a group $NR^1$ wherein $R^1$ is hydrogen, $C_{1-4}$ alkyl or a group $COR^2$ wherein $R^2$ is hydrogen, $C_{1-4}$ alkoxy or amino and the dotted line represents a single or double bond.

Y is suitably substituted by halogen atoms or alkenyl, alkenyloxy, nitro, hydroxy, cyano, mercapto, alkylthio, substituted sulphonyloxy, substituted sulphonyl, substituted sulphinyl, substituted carboxyl, optionally substituted amino, optionally substituted alkyl or optionally substituted alkoxy groups. Suitably the substituents are at one or more of the 3,4 and 6 positions.

A preferred group of compounds of the formula (II) is that wherein Y is a group:

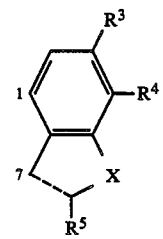

or a salt, acyl derivative or N-oxide thereof, which is linked to the pyrimidinylmethyl moiety at the 1 or 7 position, wherein X is oxygen, sulphur, $CH_2$ or a group $NR^1$ or $S(O)_n$ as hereinbefore defined, the dotted line represents a single or double bond and $R^3$, $R^4$ and $R^5$ are the same or different and each is hydrogen, halogen, $C_{2-4}$ alkenyl, $C_{2-4}$ alkenyloxy, nitro, cyano, hydroxy, mercapto, a group $-OSO_2R^6$ or $-S(O)_nR^6$ wherein $R^6$ is $C_{1-3}$ alkyl and n is 0, 1 or 2, a group $-COR^7$ wherein $R^7$ is methyl, ethyl, methoxy, ethoxy, amino, methylamino, ethylamino, dimethylamino, or diethylamino, or one or more of $R^3$, $R^4$ and $R^5$ is amino optionally substituted by one or more $C_{1-4}$ alkyl groups or the nitrogen atom forming part of a five or six-membered heterocyclic ring, $C_{1-4}$ alkyl or $C_{1-4}$ alkoxy each optionally substituted by halogen, hydroxy or $C_{1-2}$ alkoxy or $R^3$ and $R^4$ form a methylenedioxy group. Suitably $R^5$ is not halogen, hydroxy or alkoxy when X is oxygen, sulphur or a group $NR^1$.

Most suitably X is oxygen, sulphur or a group $NR^1$ or $S(O)_n$. Suitably $R^3$ and $R^4$ are the same or different and each is hydrogen, methyl, methoxy, amino, dimethylamino, methylthio, bromo or chloro and most suitably $R^3$ and $R^4$ are the same or different and each is hydrogen, methoxy or dimethylamino. It is preferred that $R^3$ and $R^4$ are not both hydrogen.

Suitably $R^5$ is hydrogen or methyl.

Suitably R¹ is methyl. Suitably the dotted line represents a double bond. One preferred group of compounds of the present invention is that of the formula (III):

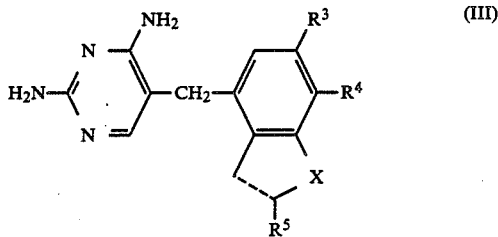

or a salt, N-oxide or acyl derivatives thereof, wherein X, R¹ to R⁵ and the dotted line are as hereinbefore defined.

A further preferred group of compounds of its present invention is that of the formula (IV):

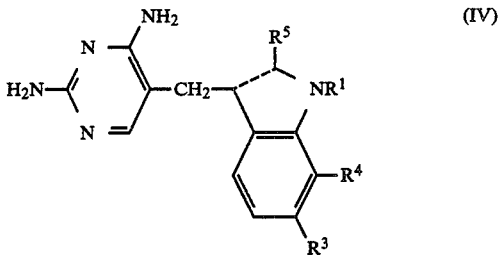

or a salt, N-oxide or acyl derivative thereof, wherein X and R¹ to R⁵ are as hereinbefore defined.

Particularly preferred compounds of the present invention include: 2,4-diamino-5-(6,7-dimethoxy-2-methyl-4-benzofuranylmethyl)pyrimidine and 2,4-diamino-5-[(6,7-dimethoxybenzo[b]thien-4-yl)methyl]pyrimidine.

The compounds of the formula (II) are bases and, as such, form acid addition salts with acids. Suitable acid addition salts of the compounds of the formula include those formed with both organic and inorganic acids. Such acid addition salts will normally be pharmaceutically acceptable. Thus, preferred salts include those formed from hydrochloric, sulphuric, citric, tartaric, phosphoric, lactic, benzoic, glutamic, aspartic, pyruvic, acetic, succinic, fumaric, maleic, oxaloacetic, isethionic, stearic, fumaric, methanesulphonic, p-toluenesulphonic, lactobionic and glucuronic acids.

Suitable acyl derivatives are those wherein an amino group is substituted by a group —COM wherein M is hydrogen or $C_{1-11}$ alkyl or $C_{2-11}$ alkenyl, preferably $C_{1-4}$ alkyl or $C_{2-4}$ alkenyl, optionally substituted by carboxy, carb-$C_{1-4}$ alkoxy, nitrile, amino, chlorine or phenoxy optionally substituted by halogen, methyl or methoxy, the alkyl or alkenyl groups being optionally interspersed with one or more oxygen atoms or forming part or the whole of a cycloaliphatic ring or may represent a $C_{6-10}$ aromatic or $C_{6-10}$ araliphatic residue optionally substituted by one or more chlorine atoms or methyl, $OCH_2COOH$, carb-$C_{1-4}$ alkoxy or a heterocyclic group containing one or more nitrogen, oxygen or sulphur atoms.

Preferred acyl derivatives are those wherein the amino group at the 2-position of the pyrimidine ring is substituted, particularly those wherein the amino group is substituted by acetyl or by an acyl group derived from an amino acid such as a glycyl group.

Suitable N-oxides of compounds of the formula (II) include those formed by oxidation of either or both of the nitrogen atoms in the pyrimidine ring or by oxidation of X when this is a nitrogen atom.

The preparation of salts, acyl derivatives and N-oxides is carried out by conventional methods well known to those skilled in the art.

Pharmaceutically acceptable acid addition salts of compounds of the formula (II) form a particularly preferred aspect of the present invention.

In a further aspect, the present invention provides a pharmaceutical composition comprising a compound of the formula (II) in combination with a pharmaceutically acceptable carrier. By the terms "pharmaceutical composition" and "pharmaceutically acceptable carrier" are meant those compositions and carriers suitable for use in human and/or veterinary medicine.

The compounds of the formula (II) can conveniently be presented in the compositions of the present invention in an effective unit dosage form, that is to say in an amount sufficient to be effective against the bacterial organism in vivo.

The pharmaceutically acceptable carriers present in the compositions of the present invention are materials recommended for the purpose of administering the medicament. These may be liquid, solid or gaseous materials, which are otherwise inert or medically acceptable and are compatible with the active ingredient.

These pharmaceutical compositions may be given parenterally, orally, used as a suppository, applied as an ophthalmic solution, or applied topically as an ointment, cream or powder. However, oral and parenteral administration of the compositions is preferred for human use. For veterinary use, intramammary as well as oral and parenteral administration is preferred.

For oral administration, fine powders or granules will contain diluting, dispersing and/or surface active agents, and may be presented in a draught, in water or in a syrup, in capsules or cachets in the dry state or in a non-aqueous suspension wherein suspending agents may be included, or in a suspension in water or syrup. Where desirable or necessary, flavouring, preserving, suspending, thickening or emulsifying agents can be included.

For parenteral administration, the compounds may be presented in sterile aqueous injection solutions which may contain antioxidants or buffers.

As stated above, free base or a salt thereof may be administered in its pure form unassociated with other additives in which case a capsule or cachet is the preferred carrier.

Other compounds which may be included are, for example, medically inert ingredients, e.g. solid and liquid diluents such as lactose, glucose, starch or calcium phosphate for tablets or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Alternatively the active compound may be presented in a pure form as an effective unit dosage, for instance, compressed as a tablet or the like.

For veterinary use, different intramammary formulations will normally be prepared for use in dry cows and for use in milking cows. Thus, formulations for dry cow use will normally be in an oil, such as peanut oil, gelled with a gelling agent such as aluminium monostearate. Formulations for milking cow use will usually contain an emulsifying agent (for example Tween 20 or a polysorbate) and a milk miscible carrier such as peanut oil or a mineral oil.

It may be advantageous to include the compounds of formula (II) in a pharmaceutical composition which includes other active ingredients for example p-aminobenzoic acid competitors such as sulphonamides.

Of known p-aminobenzoic acid competitors, the following sulphonamide compounds (or pharmaceutically acceptable salts thereof) are particularly useful:

Sulfanilamide, Sulfadiazine, Sulfamethisazole, Sulfapyridine, Sulfathiazole, Sulfamerazine, Sulfamethazine, Sulfisoxazole, Sulformethoxine, 2-(p-Aminobenzenesulfonamide-3-methoxypyrazine (Kelfizina), Mafenide, 5-Sulfanilamido-2,4-dimethylpyrimidine, 4-($N^1$-Acetylsulfanilamido)-5,6-dimethoxypyrimidine, 3-Sulfanilamido-4,5-dimethylisoxazole, 4-Sulfanilamido-5-methoxy-6-decyloxypyrimidine sulfamonomethoxine, 4-p-(8-Hydroxyquinolinyl-4-azo)-phenylsulfanilamido-5,6-dimethoxypyrimidine, Sulfadimethoxine, Sulfadimidine, Sulfamethaxazole, Sulfamoxole, Sulfadoxine, Sulfaguanidine, Sulfathiodimethoxine, Sulfaquinoxaline, and p-(2-Methyl-8-hydroxyquinolinyl-5-azo)phenylsulfanilamido-5,6-dimethoxypyrimidine.

However, the most preferred combinations include those containing Sulfadiazine, Sulfamethoxazole, Sulfadoxine, Sulfamoxole or Sulfadimidine. The ratio of the compound of the formula (II) to sulphonamide will normally be from 3:1 to 1:10, for example 1:1 to 1:5. A particularly preferred composition of the present invention comprises a compound of formula (II) and a sulphonamide in a ratio of 1:2 to 1:5 preferably together with a pharmaceutically acceptable carrier.

Tablets or other forms of presentation provided in discrete units may conveniently contain an amount of compound of the formula (II) which is effective at a dosage or as a multiple of the same, for instance for human use, units containing 2.5 to 200 mg usually around 30 to 100 mg and for veterinary use, units containing 30 to 500 mg.

The pharmaceutical compositions of the present invention can be prepared by the admixture of a compound of the formula (II) with a pharmaceutically acceptable carrier. Other active ingredients, such as a sulfonamide, or conventional pharmaceutical excipients may be admixed as required.

The compounds of the present invention are useful for the treatment of microbial infections and, in particular, gram negative aerobic, gram positive aerobic or anaerobic bacterial infections in mammals. They are particularly useful in the treatment of Staphylococcal infections for example mastitis in cattle, Neisseria infections in humans, for example *N. gonorrhea*, acne in humans, and anaerobic infections. Most compounds also have an excellent level of general antibacterial activity.

Still another aspect of the present invention provides a method for the treatment to prophylaxis of bacterial infections in mammals by the administration of an effective non-toxic antibacterial amount of a compound of formula (II) or a pharmaceutically acceptable salt thereof, or a composition as hereinbefore described.

As indicated above, the compounds of the formula (II) are generally useful in treating bacterial infections by rectal, parenteral, topical or oral administration. The compounds of formula (II) are normally administered at a dose from 0.1 mg/kg to 30 mg/kg per day and preferably 1 mg/kg to 10 mg/kg. The dose range for adult humans is generally from 25 to 300 mg/day and preferably 100 to 200 mg/day.

The dose range for intramammary administration of the compounds of the formula (II) is generally from 100 to 500 mg, preferably 200 mg to 400 mg, per quarter of the udder to dry cows. Milking cows will normally receive four to six medications of a composition of the present invention, a dose being conveniently administered at milking time (i.e. twice daily) to each of the desired quarters of the udder. Dry cows will normally receive only one medication of a composition of the present invention, one dose being provided to each of the four quarters of the udder.

The compunds of formula (II) and their pharmaceutically acceptable salts may be prepared by methods known for the synthesis of compounds of analogous structure.

Thus the present invention provides a process for preparation of compounds of the formula (II) as hereinbefore defined which process comprises:

(a) (i) the reaction of a guanidine salt with a compound of the formula (V) or (VI):

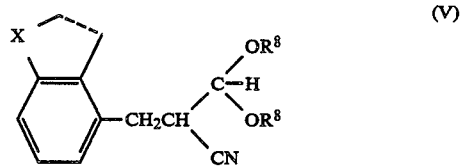

(V)

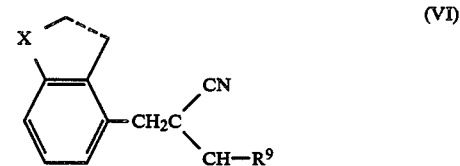

(VI)

wherein Y is as hereinbefore defined and is optionally substituted as hereinbefore defined, $R^8$ is a $C_{1-4}$ alkyl group and $R^9$ is a nucleophilic leaving group such as a $C_{1-4}$ alkoxy group, for example, a methoxy, ethoxy or methoxyethoxy group, or an amino, $C_{1-4}$ alkylamino, benzylamino, di-($C_{1-4}$)alkylamino, naphthylamino, optionally substituted anilino, morpholino, piperidino or N-methyl piperazino group and most preferably $R^9$ is an anilino group:

(ii) the reaction of a compound of the formula (VII):

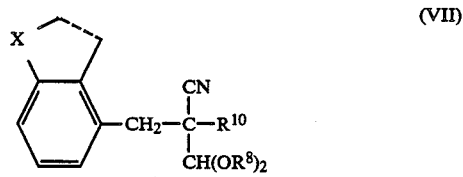

(VII)

wherein Y and $R^8$ are as hereinbefore defined and is optionally substituted as hereinbefore defined and $R^{10}$ is an alkoxycarbonyl or aldehyde group, with potassium or sodium hydroxide in a $C_{1-4}$ alkanol followed by addition of guanidine;

(iii) the reaction of a compound of the formula (VIII):

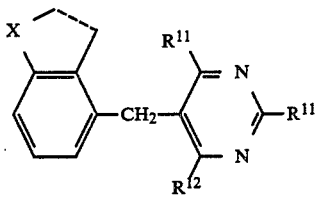

(VIII)

wherein $R^{11}$ is an amino group or a leaving group, such as a $C_{1-4}$ alkylthio group or a halogen atom, $R^{12}$ is a hydrogen or halogen atom, except that both groups $R^{11}$ cannot be amino groups and Y is as hereinbefore defined and is optionally substituted as hereinbefore defined with an aminating agent such as ammonia and thereafter when $R^{12}$ is a halogen atom removing this by hydrogenolysis;

(iv) the reaction of a compound of the formula (IX):

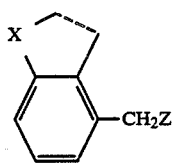

(IX)

wherein Z is a halogen atom, hydroxy, di-$C_{1-4}$ alkyl substituted amino or other leaving group and Y is as hereinbefore defined and is optionally substituted as hereinbefore defined with a compound of the formula (X):

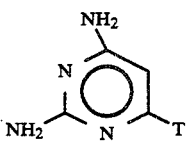

(X)

wherein T is a hydrogen, hydroxy or $C_{1-4}$ alkylthio group, and then when T is not hydrogen converting the group T to hydrogen by hydrogenolysis when T is a $C_{1-4}$ alkylthio group or, when T is a hydroxy group, by first converting it to the mesylate or tosylate derivative or to thio, alkylthio or halogen and then removing this by hydrogenolysis;

(b) when it is required to prepare a compound of the formula (III), the cyclisation of a compound of formula (XI):

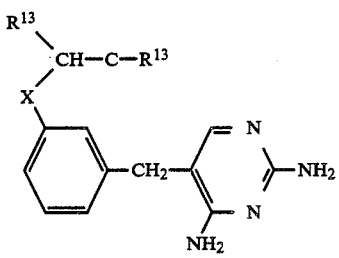

(XI)

wherein X is as hereinbefore defined and the phenyl group is optionally substituted as hereinbefore defined and the two groups $R^{13}$ are the same or different and each is hydrogen or $C_{1-4}$ alkyl;

(c) when it is required to prepare a compound of the formula (II) wherein the 4-position of the phenyl ring may be substituted by hydroxy, alkoxy, amino or substituted amino the reaction of a compound of the formula (XII):

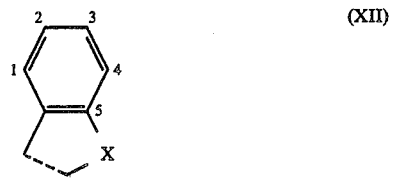

(XII)

wherein the 4-position of the phenyl ring is optionally substituted by hydroxy, alkoxy, amino, substituted amino and the $\widehat{X}$ ring being optionally substituted by other substituents as hereinbefore defined with 2,4-diamino-5-hydroxymethylpyrimidine;

(d) the conversion of one compound of the formula (II) to a different compound of the formula (II) for example by the reduction of the double bonds, conversion of a hydroxy group to $C_{1-4}$ alkylthio group or an optionally substituted $C_{1-4}$ alkoxyl group or conversion of an amino group to a $C_{1-4}$ alkylthio group or hydrogen, halogen, hydroxy or cyano via a diazo group or to a substituted amino group by methods well known to those skilled in the art.

The reaction of guanidine with a compound of the formula (V) or (VI) will take place under conditions analogous to those described in U.K. Patent Nos. 1 133 766 and 1 261 455 respectively for the preparation of structurally related benzylpyrimidines. Conveniently the reaction is carried out in a $C_{1-4}$ alkanol, for example methanol or ethanol. The compounds of the formula (V) and (VI) may be prepared by methods known in the art.

The reaction of a compound of the formula (VII) with guanidine and the preparation of the compounds of the formula (VII) will be carried out by methods analogous to those described in Belgian Pat. No. 855 505.

In the compounds of the formula (VIII) when $R^{11}$ or $R^{12}$ are halogen atoms these are suitably chlorine or bromine atoms. The reaction may conveniently be carried out under the reaction conditions described in U.K. Pat. Nos. 875 562 and 1 132 082. The reduction of $R^{12}$ when this is halogen will suitably be carried out under the conditions described in German Offenlegungschrift No. 2258238. This is not a preferred method for preparing those compounds wherein $R^3$ or $R^4$ are groups that are susceptible to catalytic hydrogenation.

The compounds of formula (VIII) may be prepared by methods known in the art, for example as described in U.K. Pat. Nos. 875562 and 1132082 or German Offenlegungschrift No. 2258238. The compounds of the formula (VIII) wherein $R^{11}$ and/or $R^{12}$ are halogen atoms may conveniently be prepared from the corresponding compounds wherein $R^{11}$ and/or $R^{12}$ are hydroxy. These compounds may be prepared by methods analogous to these described in the art or by the reaction of a compound of the formula (XII) with 5-dimethylaminomethyluracil or 5-hydroxymethyluracil. This reaction will normally be carried out in an inert high boiling polar solvent, for example a high boiling $C_{2-6}$ alkanol such as ethylene glycol, at between 100° and 200° C. for example between 130° and 160° C. The reaction will nor- The compounds of the formula (XI) wherein X is sulphur or oxygen may be prepared by reaction schemes A and B respectively:

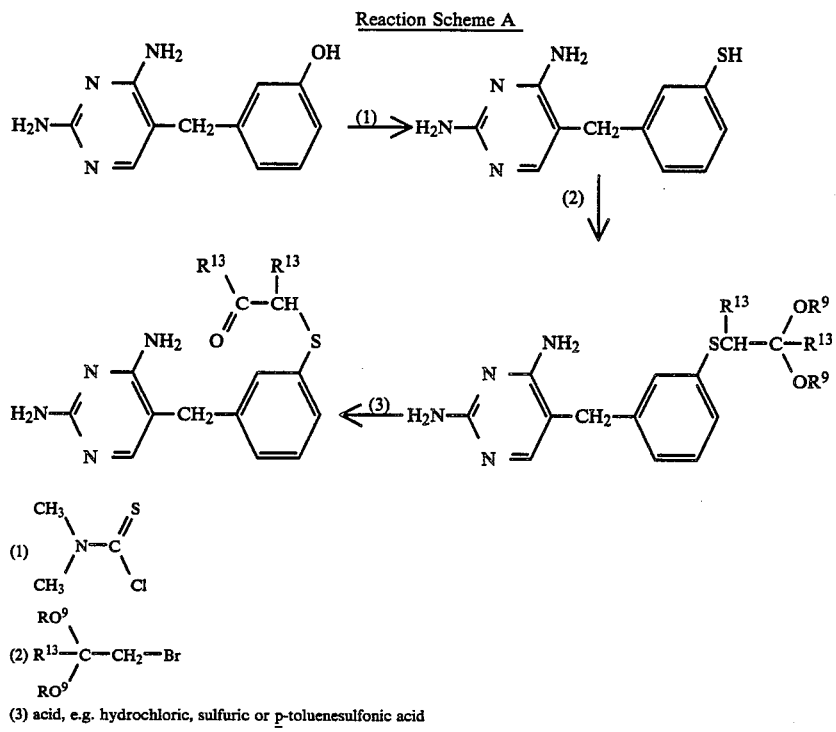

mally be carried out under basic conditions when the 4-position of the phenyl ring is substituted by hydroxy, for example in the presence of sodium methoxide, and under neutral conditions when the 4-position of the phenyl ring is substituted by amino or substituted amino.

Certain compounds of the formula (VIII) wherein the 4-position of the phenyl ring is substituted by a hydroxy group may be converted to compounds of the formula (VIII) wherein the 4-position is substituted by an alkoxy or thio $C_{1-4}$ alkyl group and certain compounds of the formula (VIII) wherein the 4-position of the phenyl ring is substituted by an amino group and $R^{11}$ is a hydroxyl group may be converted to compounds of the formula (VIII) wherein the 4-position of the phenyl ring is substituted by $C_{1-4}$ alkylthio, halogen, cyano, substituted amino group or hydrogen by methods well known to those skilled in the art.

Suitably Z is a dialkylamino or cyclic amino group containing up to 10 carbon atoms; a dimethylamino group is particularly convenient. The reaction will be carried out under conditions well known to those skilled in the art of Mannich reactions. It has been found that the reaction may suitably be carried out at an elevated temperature, suitably between 100° and 200° C. in a solvent having a suitably high boiling point, for example a glycol such as ethylene glycol. The dethiation is suitably carried out by hydrogenolysis in the presence of a transition metal catalyst; Raney nickel is particularly suitable for this purpose. This reaction will normally be carried out in a polar solvent, for example $C_{1-4}$ alkanol such as methanol or ethanol.

Again, this is not a preferred method of preparing those compounds of the formula (II) wherein there are groups that are susceptible to a catalytic hydrogenation.

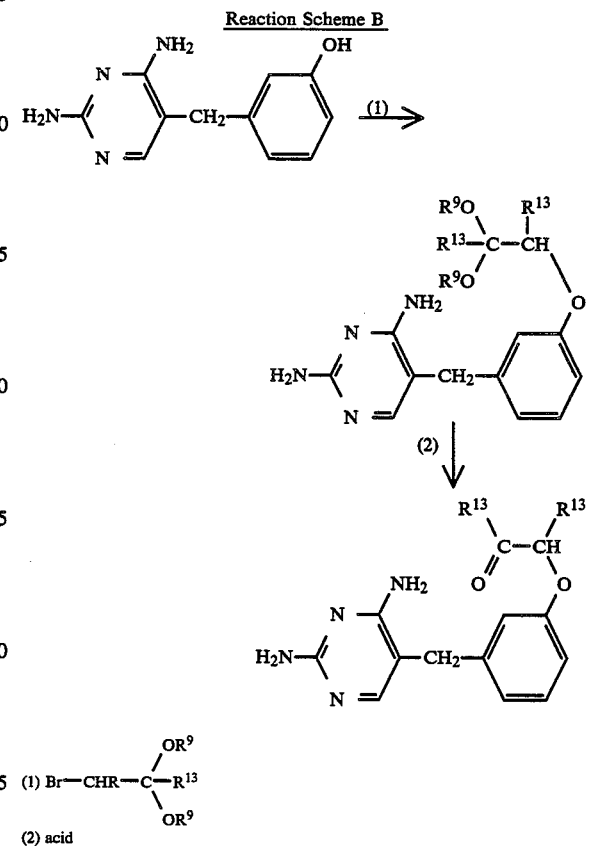

The compounds of the formula (XII) wherein X is other than oxygen or sulphur will be made by methods analogous to those described in the art.

The cyclisation of a compound of the formula (XI) will take place under conventional conditions, for example those described in "The Chemistry of Heterocyclic Compounds," Wiley-Interscience, John Wiley & Sons, Inc., N.Y.: *The Indoles,* Part One, vol. 25, p. 317 ff (1972); "Heterocyclic Compounds," vol. 2, R. C. Elderfield, ed., John Wiley & Sons, Inc., N.Y., p. 11 ff, p. 146 ff (1951); "Advances in Heterocyclic Chemistry," vol. 11, A. R. Katritzky and A. J. Boulton, ed., Academic Press, N.Y., p. 217 ff (1970); and "Advances in Heterocyclic Chemistry," vol. 18, A. R. Katritzky and A. J. Boulton, ed., Academic Press, N.Y., p. 362 ff (1975). It is preferred that the phenyl ring be suitably substituted in order that cyclisation proceeds at the 2-position.

The preparation of a compound of the formula (XI) from the corresponding acetal and its conversion to the corresponding compound of formula (II) will conveniently take place in situ.

The reaction of a compound of the formula (XII) with 2,4-diamino-5-hydroxymethylpyrimidine will normally be carried out under the reaction conditions described in U.K. Pat. No. 1413471. Thus the reaction will conveniently be carried out in a polar solvent capable of dissolving both reactants at a non-extreme temperature, for example between 50° C. and 150° C. The reaction is preferably carried out in the presence of a strong acid catalyst, such as hydrochloric, acetic, methanesulphonic or p-toluenesulphonic acids.

In the case where there is an alkoxy group at the 4-position, it may be necessary to separate the desired compound of the formula (III) from other substances present in the reaction mixture.

It will be apparent to those skilled in the art that when certain ring substituents are present in the final compounds of the formula (II) certain methods of preparation will preferably not be used to make these compounds due to the possibility of the reaction conditions changing the final product group, for example hydrogenolysis or addition across the double bond when a double bond is present.

Certain compounds of the formula (II) whilst having some antibacterial activity in their own right are also useful as intermediates in the preparation of other compounds of the formula (II) having interesting antibacterial activity. The intermediates of the formula (V) to (IX), and (XI) which are novel form a further aspect of the present invention.

In yet another aspect, the present invention provides the first use of the compounds of the formula (II) in human and veterinary medicine. The preferred human use of the compounds of the formula (II) is in the treatment or prophylaxis of bacterial infections.

The following examples illustrate the preparation of the compounds of the present invention and their pharmacological properties. All temperatures are in degrees centigrade.

PHARMACOLOGICAL DATA

The compounds of the present invention were subjected to standard tests in order to determine the minimum inhibitory concentration in μg/ml needed to inhibit a range of bacterial microorganisms in-vitro and the amount needed to give 50% inhibition of the dihydrofolate reductase enzyme from *E. coli.*

| Compound | |
|---|---|
| TMP | 2,4-Diamino-5-(3,4,5-trimethoxybenzyl)pyrimidine |
| 1 | 2,4-Diamino-5-(6,7-dimethoxy-2,3-dimethyl-4-benzofuranylmethyl)pyrimidine |
| 2 | 2,4-Diamino-5-(2,3-dihydro-6,7-dimethoxy-2-methyl-4-benzofuranyl)pyrimidine |
| 3 | 2,4-Diamino-5-(6,7-dimethoxy-2-methyl-4-benzofuranylmethyl)pyrimidine |

TABLE I

| MIC Organisms | Minimum Inhibitory Concentrations (μg/ml) | | | |
|---|---|---|---|---|
| | TMP | 1 | 2 | 3 |
| St. pyogenes CN10 | 0.5 | 5.0 | 0.5 | 0.05 |
| St. faecalis CN478 | 0.1 | 0.5 | 0.05 | 0.05 |
| St. agalactiae CN1143 | 0.5 | 5.0 | 0.5 | 0.05 |
| Staph. aureus CN491 | 0.5 | 0.5 | 0.5 | 0.05 |
| Esch. coli CN314 | 0.05 | 0.5 | 0.5 | 0.5 |
| N. gonorrhoeae (mean of 17 strains) | 40 | 25 | — | 2.8 |
| B. fragilis (mean of 3 Strains) | 3.1 | 25 | 6.2 | 0.6 |

EXAMPLE 1

A.

2,4-Diamino-5-(3,4-dimethoxy-5-(1-methyl-2-oxopropoxy)benzyl)pyrimidine

To a solution of 2.76 g (0.01 mole) of 2,4-diamino-5-(3-hydroxy-4,5-dimethoxybenzyl)pyrimidine (D. E. Schwartz, W. Vetter, and G. Englert, *Arzneim.-Forsch.* (Drug Res.) 1970, 20, 1867; G. Rey-Bellet and R. Reiner, *Helv. Chim. Acta* 1970, 53, 945) in 40 mL of dry dimethyl sulfoxide was added 1.12 g (0.01 mole) of potassium t-butoxide. To the resulting suspension was added in one portion 1.16 g (0.0109 mole) of 3-chloro-2-butanone. The mixture was stirred at room temperature for 1 hour. The solvent was removed under vacuum and the residue was partitioned between 100 mL of methylene chloride and 100 mL of 0.1N sodium hydroxide. The organic layer was separated and the aqueous layer was extracted with an additional 100 mL of methylene chloride. The organic layers were combined, washed with 100 mL of water, dried (MgSO$_4$) and concentrated to give a quantitative yield (3.58 g) of the title compound. Recrystallization from 95% ethanol gave an analytical sample; mp 167.5°–168.5°. Anal. Calc'd for C$_{17}$H$_{22}$N$_4$O$_4$: C, 58.95; H, 6.40; N, 16.17. Found: C, 58.77; H, 6.42; N, 16.13.

B.

2,4-Diamino-5-(6,7-dimethoxy-2,3-dimethyl-4-benzofuranylmethyl)pyrimidine

A mixture of 0.70 g (0.002 mole) of 2,4-diamino-5-(3,4-dimethoxy-5-(1-methyl-2oxopropoxy)benzyl)-pyrimidine in 11 g of polyphosphoric acid was stirred and heated on a steam bath for 20 minutes then poured onto 100 g of ice. The resulting mixture was basified with concentrated ammonium hydroxide, then extracted with methylene chloride (100 mL). The extract was washed with water (150 mL), dried over anhydrous magnesium sulfate and concentrated in vacuo to give the title compound (0.52 g, 78%). Recrystallization from absolute ethanol gave an analytical sample; mp>249° dec. Anal. Calcd for C$_{17}$H$_{20}$N$_4$O$_3$: C, 62.18, H, 6.14; N, 17.06. Found: C, 62.01; H, 6.17, N, 17.01.

EXAMPLE 2

A.
5-(3-Allyloxy-4,5-dimethoxybenzyl)-2,4-diaminopyrimidine

The title compound was prepared from 2,4-diamino-5-(3-hydroxy-4,5-dimethoxybenzyl)pyrimidine (20.0 g, 72.4 mmol) and allyl bromide by the procedure of Example 1A. Recrystallization from 95% ethanol gave title compound as white crystals (14.9 g); mp 160°–162°. Anal. Calcd for $C_{16}H_{20}N_4O_3$: C, 60.74; H, 6.37; N, 17.71. Found: C, 60.94; H, 6.45; N, 17.62.

B.
5-(2-Allyl-3-hydroxy-4,5-dimethoxybenzyl)-2,4-diaminopyrimidine

A mixture of 5-(3-allyloxy-4,5-dimethoxybenzyl)-2,4-diaminopyrimidine (14.6 g, 46.2 mmol) and N,N-diethylaniline was maintained at 190' (oil bath) under nitrogen for 3.5 h. The resulting solution was cooled and the gummy precipitate slurried with 95% EtOH to give an off-white solid (5.1 g), mp 213°–214° dec, which TLC on silica gel with MeOH:CH$_2$Cl$_2$/1:4 showed to be identical to the analytical sample. One recrystallization from 95% EtOH gave white crystals of the title compound, mp 217°–218° dec. Anal. Calcd for $C_{16}H_{20}N_4O_3$: C, 60.74; H, 6.37; N, 17.71. Found: C, 60.70; H, 6.40; N, 17.70. Chromatography of combined mother liquors gave additional title compound (8.7 g).

C.
2,4-Diamino-5-(2,3-dihydro-6,7-dimethoxy-2-methyl-4-benzofuranylmethyl)-pyrimidine A mixture of 5-(2-allyl-3-hydroxy-4,5-dimethoxybenzyl)-2,4-diaminopyrimidine (1.50 g, 4.74 mmol) and polyphosphoric acid (50 g) was heated to 95° and maintained at this temperature with stirring until a clear pale yellow syrup was achieved (about 1 h). This syrup was poured into ice-water and the resulting solution basified with ammonium hydroxide. The resulting white solid (1.3 g) was chromatographed on silica gel eluted with MeOH:CH$_2$Cl$_2$/1:9 to give the title compound as white powder (1.2 g). Recrystallization from 95% ethanol gave clusters of white needles, mp 216°–219°. Anal. Calcd for $C_{16}H_{20}N_4O_3$ (316.37); C, 60.74; H, 6.37; N, 17.71. Found: C, 60.48; H, 6.41; N, 17.63.

EXAMPLE 3

A.
2,4-Diamino-5-[3,4-dimethoxy-5-(2-propynyloxy)benzyl]pyrimidine

The title compound was prepared from 2,4-diamino-5-(3-hydroxy-4,5-dimethoxybenzyl)pyrimidine and propargyl chloride by the procedure of Example 1A. Recrystallization from 95% ethanol gave off-white needles (73%); mp 160°–161°. Anal. Calcd for $C_{16}H_{18}N_4O_3$: C, 61.13; H, 5.77; N, 17.82. Found: C, 60.96; H, 5.80; N, 17.75.

B.
2,4-Diamino-5-(6,7-dimethoxy-2-methyl-4-benzofuranylmethyl)pyrimidine A mixture of 2,4-diamino-5-[3,4-dimethoxy-5-(2-propynyloxy)benzyl]pyrimidine (1.18 g, 3.75 mmol), potassium carbonate (0.518 g, 3.75 mmol) and sulfolane (10 mL) was heated to 220°–230° under nitrogen over a period of 20 minutes and then maintained at this temperature for an additional 15 minutes. The resulting dark mixture was cooled and the precipitate was adsorbed on silica gel. The title compound was eluted with MeOH:CH$_2$Cl$_2$/1:9 as an off-white powder, after recrystallization from 95% ethanol; mp 209°–212°. Anal. Calcd for $C_{16}H_{18}N_4O_3 \cdot \frac{1}{2}H_2O$: C, 59.43; H, 5.92; N, 17.33. Found: C, 59.22; H, 5.97; N, 17.31.

EXAMPLE 4

A. 3-Anilino-2-(1-methyl-3-indolylmethyl)acrylonitrile

To a solution under nitrogen of 6.5 g (0.044 mole) of 3-anilinopropionitrile in 20 mL of dimethylsulfoxide was added 2.4 g (0.044 mole) of sodium methoxide. After stirring for 5 min, 6.5 g (0.41 mole) of 1-methylindole-3-carboxaldehyde. (E. Wenkert, J. H. Udelhofen and N. K. Bhattacharya, *J. Am. Chem. Soc.*, 1959, 81, 3763) was added to the mixture which was then heated at 135° for 30 min, followed by cooling and dilution with 200 mL of water. The resulting solid was collected, resuspended in 150 mL of water and collected again giving 9.14 g (78%) of the title compound; the structure was confirmed by $^1$H-NMR.

B.
2,4-Diamino-5-(1-methyl-3-indolylmethyl)pyrimidine

To 100 mL of an ethanolic guanidine solution prepared from 2.10 g (0.022 mole) of guanidine hydrochloride and 1.20 g (0.022 mole) of sodium methoxide was added 5.00 g (0.017 mole) of 3-anilino-2-(1-methyl-3-indolylmethyl)acrylonitrile. The solution was heated under reflux for ½ hour and then 100 mL of 2-methoxyethanol was added. The internal temperature was allowed to gradually increase to 120° by distillation of the ethanol, after which it was heated at this temperature for 4.75 hr. The reaction was cooled and the solvent was removed in vacuo. The residue was recrystallized from 95% ethanol to give two crops of the title compound (total 1.82 g, 41%) mp 253°–256° dec. Anal. Calcd for $C_{14}H_{15}N_5$: C, 66.38, H, 5.97; N, 27.65. Found: C, 66.05; H, 6.04; N, 27.89.

EXAMPLE 5

A.
3-Anilino-2-(5-methoxy-1-methyl-3-indolylmethyl)acrylonitrile

The title compound was prepared from 5-methoxy-1-methylindole-3-carboxaldehyde (S. Misztal, *Dessert. Pharm. Pharmacol.*, 1972, 24, 509) and 3-anilinopropionitrile by the procedure of Example 4A (71%); the structure was confirmed by $^1$H-NMR.

B.
2,4-Diamino-5-(5-methoxy-1-methyl-3-indolylmethyl)-pyrimidine

The product of Example 5A was used in the procedure of Example 4B to give the title compound (49%) mp 195°–198° dec. Anal. Calcd for $C_{15}H_{17}N_5O \cdot \frac{1}{4}H_2O$: C, 62.59; H, 6.13; N, 24.33. Found: C, 62.48; H, 6.12, N, 24.29.

EXAMPLE 6

A. 3-Anilino-2-(3-benzo[b]thienylmethyl)acrylonitrile

The title compound was prepared from thianaphthene-3-carboxaldehyde (W. J. King and F. F. Nord, *J. Org. Chem.* 1948, 13, 635) and 3-anilinopropionitrile by the procedure of Example 4A (29%); mp 168°–170° dec. Anal. Calcd for $C_{18}H_{14}N_2S \cdot 0.1\ H_2O$: C, 73.99; H, 4.90;

N, 9.59; S, 10.97. Found: C, 74.03; H, 5.21; N, 9.59; S, 11.01.

B. 2,4-Diamino-5-(3-benzo[b]thienylmethyl)pyrimidine

The title compound was prepared from 3-anilino-2-(benzo[b]thienylmethyl)-acrylonitrile by the procedure of Example 4B (80%); mp 220°–222°; the structure was confirmed by $^1$H-NMR. Anal. Calcd for $C_{13}H_{12}N_4S$: C, 60.91; H, 4.72; N, 21.86; S, 12.51. Found: C, 61.04; H, 4.78; N, 21.79; S, 12.56.

EXAMPLE 7

Preparation of
2,4-Diamino-5-[(6,7-dimethoxybenzo[b]thien-4-yl)methyl]pyrimidine A. 1,2-Dimethoxy-3-(2,2-diethoxyethylthio)benzene To a flask equipped with addition funnel, Gooch tube, thermometer, condenser, and nitrogen inlet, was added 6.71 g (0.04 mol) of veratrole in 75 ml of dry tetrahydofuran. A solution of n-butyl lithium (27.5 ml, 0.044 mol), 1.6M in hexane, was added dropwise over a 20 minute period at room temperature. The mixture was stirred for two hours, and chilled to 5° C., followed by the addition of 1.41 g (0.044 mol) of sulfur from an Erlenmeyer flask attached to the Gooch tube. The mixture was allowed to reach room temperature and stirred for 30 minutes, followed by the addition of 6.62 ml (0.044 mol) of bromoacetaldehyde diethyl acetal. This mixture was allowed to stir at room temperature for three hours, and then heated at 80° for 17 hours. The reaction mixture was then added to 100 ml of water. The tetrahydrofuran layer was separated and evaporated. There remained 11.9 g of dark brown oil, which was purified by column chromatography on silica gel, using heptane:dichloromethane/1:4, then dichloromethane, then chloroform:methanol/19:1, which gave 5.47 g (48%) of compound A as an oil. Analysis: Calc. for $C_{14}H_{22}SO_4$: C, 58.72; H, 7.74; S, 11.20. Found: C, 58.61; H, 7.79; S, 11.27. MS: 286 (M+). NMR (CDCl$_3$) δ1.17 (tr, 6, CH$_2$CH$_3$)$_2$); 3.08 (d, 2, CH$_2$CH); 3.58 (d-qt, 4, (OCH$_2$Me)$_2$); 3.82 (d, 6, (OMe)$_2$); 4.64 (tr, 1, CH$_2$CH); 6.91 (s plus sh, 3, Ar).

B 6,7-Dimethoxybenzo(b)thiophene

To 2.04 g (7.1 mmol) of compound A and 30 ml of dioxane was added 0.5 ml of concentrated sulfuric acid, in a nitrogen atmosphere. The mixture was heated at 100° C. for 1.5 hours, followed by the addition of 0.3 ml more of concentrated sulfuric acid. After heating for an addition hour, the mixture was cooled, followed by the addition of 50 ml of water. The mixture was neutralized with concentrated ammonium hydroxide and extracted into dichloromethane, followed by drying over magnesium sulfate, and removal of the solvent. The product was purified by column chromatography on silica gel, using hexane:dichloromethane/2:1, which resulted in the separation of 1.02 g (60%) of product B as an oil. Anal. Calcd, for $C_{10}H_{10}O_2S$: C, 61.83; H, 5.19; S, 16.51. Found: C, 61.91; H, 5.25; S, 16.41. MS: 194 (M+), 179 (M-Me). NMR (CDCl$_3$): δ3.93 (s, 3, OMe); 4.03 (s, 3, OMe); 7.06 (d, 1, ArH, J=8.6); 7.25 (d, 2, CH=CH, J=5–6); 7.48 (d, 1, ArH, J=8.6 Hz).

C.
2,4-Diamino-5-[(6,7-dimethoxybenzo[b]thien-4-yl)methyl]pyrimidine

A mixture of 0.45 g (2.3 mmol) of product B and 0.32 g (2.3 mmol) of 2,4-diamino-5-hydroxymethylpyrimidine was added to 10 ml of glacial acetic acid and 0.4 ml (4.6 mmol) of concentrated hydrochloric acid, and refluxed for 6 hours. The solvents were evaporated, 50 ml of water was added, and the mixture was neutralized with concentrated aqueous ammonia to about pH 9. The product was extracted into dichloromethane:methanol/3:1 three times using 50 ml portions, followed by drying over MgSO$_4$, filtration, and evaporation of the solvents. The residue, 0.53 g, was purified by column chromatography on silica gel, using hexane:dichloromethane/1:1, dichloromethane, and then dichloromethane:methanol/9:1 and 5:1. A 0.19 g fraction of recovered starting material (B) was recovered, and 0.22 g of a mixture containing the title compound as ascertained by NMR spectroscopy. This mixture was separated by fractional crystallization from methanol. After separating the least soluble fraction, the more soluble fraction was concentrated and allowed to stand overnight. A crystalline product was isolated with a mp of 230°–231°. This was shown to be essentially a single substance by NMR spectroscopy; the pyrimidylmethyl attachment was found to be in the benzene ring, since there was a loss of one of the ortho-coupled protons with a J value of 8.6, whereas the pair of doublets from the thiophene ring remained (J=5.44 Hz). Nuclear overhauser NMR studies led to the assignment of the title structure (Cl) as the 4-substituted isomer. NMR (Me$_2$SO-d$_6$) δ3.84 (s, 3, 7-OMe); 3.89 (s, 5, 6-OMe plus CH$_2$); 5.72 (br. s, 2, pyrimidine NH$_2$); 6.23 (br. s, 2, pyrimidine NH$_2$); 7.05 (s, 1, Ar, H-5); 7.34 (s, 1, pyrimidine H-6); 7.39 (d, 1, Ar H-3, J=5.44 Hz); 7.55 (s, 1, Ar H-3, J=5.44 Hz). Irradiation of the singlet at 3.89 ppm (6-OMe plus CH$_2$) resulted in N.O.E. enhancements for H(3), H(5), and H(6'), indicating that this is the desired compound.

EXAMPLE 8 TABLETS

| Ingredient | Amount per tablet (mg) | |
|---|---|---|
| | Single Active Ingredient | Combination |
| 2,4-Diamino-5-(6,7-dimethoxy-2-methyl-4-benzofuranylmethyl)-pyrimidine | 100.0 | 80.0 |
| Sulfamethoxazole | — | 400.0 |
| Lactose | 84.0 | 100.0 |
| Potato starch, dried | 14.3 | 18.0 |
| Magnesium stearate | 0.7 | 1.0 |
| Polyvinylpyrrolidone | 1.0 | 1.0 |

The 2,4-diamino-5-(6,7-dimethoxy-2-methyl-4-benzofuranylmethyl)pyrimidine, lactose and potato starch (and sulfamethoxazole in the combination formulation) are mixed together and then granulated with aqueous polyvinylpyrrolidone. The granules are dried, mixed with the magnesium stearate and then compressed to produce tablets weighing 200 mg each (single active ingredient) or 600 mg each (combination).

EXAMPLE 9 CAPSULES

| Ingredient | Amount per capsule (mg) | |
|---|---|---|
| | Single Active Ingredient | Combination |
| 2,4-Diamino-5-(1-methyl-3-indolylmethyl)pyrimidine | 100.0 | 80.0 |
| Sulfisoxazole | — | 160.0 |
| Lactose | 149.0 | 79.0 |

| | Amount per capsule (mg) | |
|---|---|---|
| Ingredient | Single Active Ingredient | Combination |
| Corn starch | 149.0 | 79.0 |
| Stearic acid | 2.0 | 2.0 |

The ingredients are thoroughly mixed and then loaded into hard gelatin capsules containing 400 mg each.

EXAMPLE 10

2,4-Diamino-5-((6,7-dimethoxybenzo[b]thien-4-yl)methyl)pyrimidine

A.
3-(2,2-diethoxyethylthio)-4,5-dimethoxybenzaldehyde

Morpholine (2.61 g, 0.03 mol) and 50 ml of dry tetrahydrofuran were placed in a flame-dried three neck flask under nitrogen, and chilled to $-70°$ C. Then n-butyl lithium (20.6 ml, 0.033 mol, 1.6M in hexane) was added dropwise via an addition funnel, keeping the temperature at $-70°$. Then 5-bromo-3,4-dimethoxybenzaldehyde dissolved in 25 ml of tetrahydrofuran was added slowly, and then the reaction was stirred for 1 hour at $-50°$ C. A second equivalent of n-butyl lithium (20.6 ml, 0.033 mol) was then added, followed by sulfur (1.06 g, 0.033 mol) via a Gooch tube, and the reaction was stirred for 1 hour. Then the reaction was poured onto cold water, acidified to pH 5 with 1N hydrochloric acid, and extracted with ethyl acetate and evaporated to give 3.33 g (56% yield) of crude 3,4-dimethoxy-5-mercaptobenzaldehyde.

The crude mercaptobenzaldehyde from above (2.78 g, 14 mmol) was slurried in 1.25 ml of absolute ethanol under nitrogen. The sodium methylate (0.82 g, 15.4 mmol) was added, the reaction was stirred 10 minutes, followed by the addition of 2.69 g (14 mmol) of bromoacetaldehyde-diethylacetal. The reaction was refluxed overnight, poured into water, and extracted with ethyl acetate and evaporated to give 2.77 g of an orange oil. This was purified on a silica gel column eluted with hexane:ethyl acetate/19:1 to give 1.5 g of the title compound. NMR: ($Me_2SO$-$d_6$) $\delta$1.16 (tr, 6, $Me_2$), 3.19 (d, 2, $SCH_2$), 3.63 (double quartet, 4, ($CH_2Me$)$_2$), 3.88 (s, 3, OMe), 3.94 (s, 3, OMe), 4.69 (tr, 1, $\overline{CH}$-$CH_2$), 7.43 (d, 1, Ar), 7.56 (d, 1, Ar), 9.91 (s, 1, $\overline{CHO}$). Anal. Calcd for $C_{15}H_{22}O_5S$: C, 57.30; H, 7.05; S, 10.20. Found: C, 57.40; H, 7.05; S, 10.13.

B.
2,4-Diamino-5-(3-(2,2-diethoxyethythio)-4,5-dimethoxybenzyl)pyrimidine The aldehyde from above was converted to 2-(3-2,2-diethoxyethylthio)-4,5-dimethoxybenzyl)-3-anilinoacrylonitrile with anilinopropionitrile and sodium methylate in dimethyl sulfoxide on a 2.5 mmol scale in the same manner as in Example No. 4A. The crude product from this reaction was condensed with guanidine hydrochloride and sodium methylate in ethanol as in Example 28B to give the crude product. After purification on a silica gel column eluting with ethyl acetate:methanol/9:1 to give 0.51 g (62% yield), followed by recrystallisation in 30% ethanol/water 0.15 g of the title compound was obtained, mp 117°-118°. NMR: ($CDCl_3$) $\delta$1.19 (tr, 6, $Me_2$), 3.07 (d, 2, $SCH_2CH$), 3.61 (double quartet, 4, ($\overline{CH_2}Me$)$_2$), 3.79 (s, 3, $\overline{OMe}$), 3.83 (s, 3, OMe), 4.53 (br, s, $\overline{2, NH_2}$), 4.63 (tr, 1, $SCH_2\overline{CH}$), 4.68 (br, s, 2, $NH_2$), 6.52 (d, 1, Ar), 6.75 (d, 1, Ar), $\overline{7.76}$ (s, 1, pyrimidine-$H^6$). Anal. Calcd for $C_{19}H_{28}N_4O_4S$: C, 55.86; H, 6.91; N, 13.71; S, 7.85. Found: C, 55.82; H, 6.92; N, 13.69; S, 7.87.

C.
2,4-Diamino-5-((6,7-dimethoxybenzo[b]thien-4-yl)methyl)pyrimidine

The product from section B above (0.31 g, 0.75 mmol) was refluxed in 25 ml of water and 5 ml of ethanol under nitrogen, to which was added 0.6 ml of concentrated sulfuric acid in 0.2 ml portions at 0, ¾ hour, 1.5 hour, and then heated for ½ hour longer. The reaction was neutralised to pH 9.5, extracted with methylene chloride:methanol/3:1, and evaporated. The crude product was purified on a silica gel column eluting with 3% methanol in methylene chloride to give 0.045 g of product. NMR: ($Me_2SO$-$d_6$) $\delta$3.84 (s, 3, OMe), 3.89 (s, 3, OMe), 5.68 (br, s, 2, $NH_2$), 6.17 (br, s, 2, $NH_2$), 7.05 (s, 1, Ar), 7.35 (s, 1, pyrimidine-$H^6$), 7.39 (d, 1, thieno-H, J=5.5 Hz), 7.55 (d, 1, thieno-H, J=5.5 Hz). MS 316 ($M^+$). Anal. Calcd for $C_{15}H_{16}N_4O_2S$: C, 56.95; H, 5.10; N, 17.71. Found: C, 56.88; H, 5.14; N, 17.62.

A sample from a larger scale reaction was recrystallised as the hydrochloride salt from absolute ethanol to give title compound hydrochloride, mp 280°-283° C. Anal. Calcd for $C_{15}H_{16}N_4O_2S\cdot HCl$: C, 51.06; H, 4.86; N, 15.88. Found: C, 50.96; H, 4.91; N, 15.81.

We claim:
1. A compound which is 2,4-diamino-5-(3-benzo[b]-thienylmethyl)pyrimidine or a pharmaceutically acceptable salt thereof.
2. A compound which is 2,4-diamino-5-[(6,7-dimethoxybenzo[b]thien-4-yl)methyl]pyrimidine or a pharmaceutically acceptable salt thereof.
3. A pharmaceutical composition for antibacterial use comprising an effective antibacterial amount compound of claim 1 or 2, in combination with a pharmaceutically acceptable carrier.
4. A method of treating bacterial infections in a mammal having a bacterial infection comprising the administration to said mammal of an effective antibacterial amount of the compound of claim 1 or 2.

* * * * *